(12) United States Patent
Nyce

(10) Patent No.: US 7,893,044 B2
(45) Date of Patent: Feb. 22, 2011

(54) COMPOSITION AND METHOD FOR ALTERING LEVELS OF OR SENSITIVITY TO ADENOSINE WITH ANALOGS OF DEHYDROEPIANDROSTERONE

(75) Inventor: Jonathan W. Nyce, Collegeville, PA (US)

(73) Assignee: EpiGenesis Pharmaceutical, Inc., Cranbury, NJ (US)

( * ) Notice: Subject to any disclaimer, the term of this patent is extended or adjusted under 35 U.S.C. 154(b) by 1813 days.

(21) Appl. No.: 10/923,261

(22) Filed: Aug. 20, 2004

(65) Prior Publication Data

US 2005/0085429 A1    Apr. 21, 2005

(51) Int. Cl.
A61K 31/56    (2006.01)
(52) U.S. Cl. .................................. 514/182
(58) Field of Classification Search .......... 514/182
See application file for complete search history.

(56) References Cited

U.S. PATENT DOCUMENTS

| 4,956,355 A |   | 9/1990 | Prendergast |
| 5,859,000 A | * | 1/1999 | Dowell et al. ............ 514/178 |

FOREIGN PATENT DOCUMENTS

| GB | 2 240 472 | 8/1991 |
| JP | 53 020432 | 2/1978 |
| WO | WO 93/16704 | 9/1993 |
| WO | 02/069977 | * 9/2002 |

OTHER PUBLICATIONS

Koo E., et al., "Experiences with Dehydroepiandrosterone Therapy in Steroid-Dependent Intrinsic Bronchial Asthma," Database Biosis 'Online!, 1987, pp. 1995-1997, vol. 128, No. 38, Biosciences Information Service, Philadelphia, PA, US.
Feher, K.G., et al., "Adrenocortical Function in Bronchial Asthma," Acta Medica Hungarica, 1983, pp. 125-132, vol. 40, No. 2-3, National Institue of Rheumatism and Physiotherapy, Budapest, Hungary.
Crowley S., et al., "Asthma and Adrenarche," Journal of Endocrinology, Mar. 21-24, 1994, page Abstract P10, vol. 140, No. Suppl., 13th Joint Meeting of the British Endocrine Societies, Bournemouth, England, UK.
Abou-Gharbia, et al. Synthesis of dehydroepiandrosterone sulfatide and 16 alpha-halogenated steroids. J Pharm Sci. 1981; 70(10):1154-7.

(Continued)

Primary Examiner—San-ming Hui
(74) Attorney, Agent, or Firm—Wilson Sonsini Goodrich & Rosati PC

(57) ABSTRACT

A method of treating adenosine depletion in a subject in need of such treatment is disclosed. The method comprises administering to the subject folinic acid or a pharmaceutically acceptable salt thereof in an amount effective to treat adenosine depletion. A method of treating asthma in a subject in need of such treatment is also disclosed. The method comprises administering to the subject dehydroepiandrosterone, analogs thereof, or pharmaceutically acceptable salts thereof in an amount effective to treat asthma.

1 Claim, 4 Drawing Sheets

OTHER PUBLICATIONS

Ali, et al. Adenosine-induced bronchoconstriction in an allergic rabbit model: antagonism by theophylline aerosol. Agents Actions. 1992; 37(3-4):165-7.

Bjorck, et al. Isolated bronchi from asthmatics are hyperresponsive to adenosine, which apparently acts indirectly by liberation of leukotrienes and histamine. Am Rev Respir Dis. 1992; 145(5):1087-91.

Holgate, et al. Adenosine: a positive modulator of airway inflammation in asthma. Ann N Y Acad Sci. 1991; 629:227-36.

Thorne, et al. Adenosine-induced bronchoconstriction in conscious hyperresponsive and sensitized guinea pigs. Am. J. Respir. Crit. Care Med. 1994; 149(2):392-399.

Schubert, et al. Comparative metabolic studies following the infusion of androst-4- ene-3,17-dione, testosterone phosphate and dehydroepiandrosterone phosphate. Endokrinologie. 1965;49(1-2):1-12. (Abstract only).

* cited by examiner

COMPOSITION AND METHOD FOR ALTERING LEVELS OF OR SENSITIVITY TO ADENOSINE WITH ANALOGS OF DEHYDROEPIANDROSTERONE

FIELD OF THE INVENTION

This invention concerns methods of treating adenosine depletion by the administration of folinic acid or a pharmaceutically acceptable salt thereof. This invention further concerns methods of treating asthma by administering dehydroepiandrosterone, analogs thereof, or the pharmaceutically acceptable salts thereof.

BACKGROUND OF THE INVENTION

Adenosine is a purine which contributes to intermediary metabolism and participates in the regulation of physiological activity in a variety of mammalian tissues. Adenosine participates in many local regulatory mechanisms, in particular synapses in the central nervous system (CNS) and at neuroeffector junctions in the peripheral nervous system. In the CNS, adenosine: inhibits the release of a variety of neurotransmitters, such as acetylcholine, noradrenaline, dopamine, serotonin, glutamate, and GABA; depresses neurotransmission; reduces neuronal firing to induce spinal analgesia; and possesses anxiolytic properties. See A. Pelleg and R. Porter, *Pharmacotherapy* 10(2), 157 (1990); J. Daval, et. al., *Life Sciences* 49:1435 (1991). In the heart, adenosine suppresses pacemaker activity, slows AV conduction, possesses antiarrhythmic and arrhythmogenic effects, modulates autonomic control, and triggers the synthesis and release of prostaglandins. See K. Mullane and M. William, *Adenosine and Adenosine Receptors p.* 289 (M. Williams, ed. Humana Press, 1990). Adenosine has potent vasodilatory effects and modulates vascular tone. See A Deuseen et al., *J. Pflugers Arch.* 406: 608 (1986). Adenosine is currently being used clinically for the treatment of superventricular tachycardia and other cardiac anomalies. See C. Chronister, *American Journal of Critical Care* 2(1): 41-47 (1993). Adenosine analogues are being investigated for use as anticonvulsant, anxiolytic and neuroprotective agents. See M. Higgins et al., *Pharmacy World & Science* 1.6(2): 62-68 (1994).

Adenosine has also been implicated as a primary determinant underlying the symptoms of bronchial asthma. It induces bronchoconstriction and the contraction of airway smooth muscle. See J. Thome and. K. Broadley, *American Journal of Respiratory & Critical Care Medicine* 149(2 pt. 1): 392-399 (1994); S. Ali et al., *Agents & Actions* 37(3-4): 165-167 (1992). Adenosine causes bronchoconstriction in asthmatics but not in non-asthmatics. See Bjorck et al., *American Review of Respiratory Disease* 145(5): 1087-1091 (1992); S. Holgate et al., *Annals of the New York Academy of Sciences* 629: 227-236 (1991).

In view of the foregoing, it will be readily apparent that: (i) adenosine depletion can lead to a broad variety of deleterious conditions, and that methods of treating adenosine depletion can be an extremely useful means of therapeutic intervention; and (ii) methods of inducing adenosine depletion can also be useful in treating conditions such as asthma.

SUMMARY OF THE INVENTION

Accordingly, a first aspect of the present invention is a method of treating adenosine depletion in a subject in need of such treatment. The method comprises administering to the subject folinic acid or a pharmaceutically acceptable salt thereof in an amount effective to treat the adenosine depletion. The method may be carried out on subjects afflicted with steroid-induced adenosine depletion, subjects afflicted with anxiety, subjects afflicted with a wasting disorder, or subjects afflicted with any other disorder attributable to adenosine depletion, or where an increase in adenosine levels would be therapeutically beneficial.

A second aspect of the present invention is the use of folinic acid or a pharmaceutically acceptable salt thereof for the preparation of a medicament for treating adenosine depletion in a subject in need of such treatment, as set forth above.

A third aspect of the present invention is a method of treating asthma in a subject in need of such treatment by administering to the subject dehydroepiandrosterone, an analog thereof, or a pharmaceutically acceptable salt thereof, in an amount effective to treat asthma.

A fourth aspect of the present invention is the use of dehydroepiandrosterone, an analog thereof, or a pharmaceutically acceptable salt thereof, for the manufacture of a medicament for treating asthma in a subject in need of such treatment.

Folinic acid is an intermediate product of the metabolism of folic acid; the active form into which that acid is converted in the body, ascorbic acid being a necessary factor in the conversion process. Folinic acid has been used therapeutically as an antidote to folic acid antagonists such as methotrexate which block the conversion of folic acid into folinic acid. Additionally, folinic acid has been used as an antianemic (combatting folate deficiency). See *The Merck Index, Monograph* No. 4141 (11th Ed. 1989). The use of folinic acid in patients afflicted with adenosine depletion, or in a method to therapeutically elevate adenosine levels in the brain or other organ, has heretofor neither been suggested nor described.

In some embodiments, the invention provides compositions comprising small particle size and inhalable compositions comprising DHEA, DHEA-s, or derivatives thereof, or a pharmaceutically acceptable salt thereof, as defined herein.

DETAILED DESCRIPTION OF THE INVENTION

Figure 1:
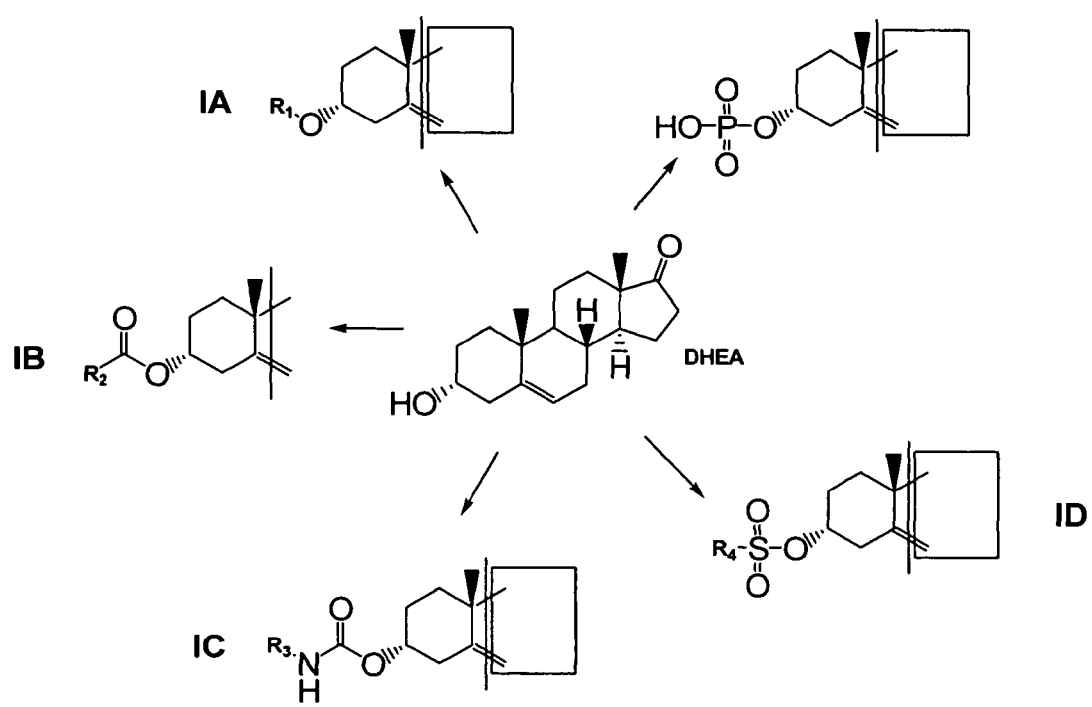
FIG. 1 depicts certain suitable analogs of DHEA.

The method of treating adenosine depletion disclosed herein can be used to treat steroid-induced adenosine depletion; to stimulate adenosine synthesis and thereby treat or control anxiety (e.g., in treating premenstrual syndrome); to increase weight gain or treat wasting disorders; and to treat other adenosine-related pathologies by administering folinic acid. Thus the term "adenosine depletion" is intended to encompass both conditions where adenosine levels are depleted in the subject as compared to previous adenosine levels in that subject, and conditions where adenosine levels are essentially the same as previous adenosine levels in that subject but, because of some other condition or alteration in that patient, a therapeutic benefit would be achieved in the patient by increased adenosine levels as compared to previous levels. Preferably, the method is carried out on patients where adenosine levels are depleted as compared to previous adenosine levels in that subject. The present invention is concerned primarily with the treatment of human subjects but may also be employed for the treatment of other mammalian subjects, such as dogs and cats, for veterinary purposes.

Folinic acid and the pharmaceutically acceptable salts thereof (hereafter sometimes referred to as "active compounds") are known, and can be made in accordance with known procedures. See generally The Merck Index, Monograph No. 4141 (11th Ed. 1989); T.S. U.S. Pat. No. 2,741,608.

Pharmaceutically acceptable salts should be both pharmacologically and pharmaceutically acceptable. Such pharmacologically and pharmaceutically acceptable salts can be prepared as alkaline metal or alkaline earth salts, such as sodium, potassium or calcium salts, of the carboxylic acid group of Folinic acid. The calcium salt of folinic acid is a preferred pharmaceutically acceptable salt.

The active compounds are preferably administered to the subject as a pharmaceutical composition. Pharmaceutical compositions for use in the present invention include those suitable for inhalation, oral, topical, (including buccal, sub-lingual, dermal and intraocular) parenteral (including subcutaneous, intradermal, intramuscular, intravenous and intraarticular) and transdermal administration. The compositions may conveniently be presented in unit dosage form and may be prepared by any of the methods well known in the art.

Compositions suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such compositions may be prepared by any suitable method of pharmacy which includes the step of bringing into association the active compound and a suitable carrier. In general, the compositions of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder. Compositions for oral administration may optionally include enteric coatings known in the art to prevent degradation of the compositions in the stomach and provide release of the drug in the small intestine.

Compositions suitable for buccal (sub-lingual) administration include lozenges comprising the active compound in a flavored base, usually sucrose and acacia or tragacanth; and pastilles comprising the compound in an inert base such as gelatin and glycerin or sucrose and acacia.

Compositions suitable for parenteral administration comprise sterile aqueous and non-aqueous injection solutions of the active compound, which preparations are preferably isotonic with the blood of the intended recipient. These preparations may contain antioxidants, buffers, bacteriostats and solutes which render the compositions isotonic with the blood of the intended recipient. Aqueous and non-aqueous sterile suspensions may include suspending agents and thickening agents. The compositions may be presented in unit-dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described.

Compositions suitable for topical application to the skin preferably take the form of an ointment, cream, lotion, paste, gel, spray, aerosol, or oil. Carriers which may be used include vaseline, lanoline, polyethylene glycols, alcohols, transdermal enhancers, and combinations of two or more thereof.

Compositions suitable for transdermal administration may be presented as discrete patches adapted to remain in intimate contact with the epidermis of the recipient for a prolonged period of time. Compositions suitable for transdermal administration may also be delivered by iontophoresis (see, e.g., *Pharmaceutical Research* 3, 318 (1986)) and typically take the form of an optionally buffered aqueous solution of the active compound.

Dosage will vary depending on age, weight, and condition of the subject. Treatment may be initiated with small dosages less than optimum dose and increased until the optimum effect under the circumstances is reached in general, the dosage will be from 1, 5, 10 or 20 mg/kg subject body weight, up to 100, 200, 500 or 1000 mg/kg subject body weight. Currently, dosages of from 5 to 500 mg/kg are preferred, dosages of from 10 to 200 mg/kg are more preferred, and dosages of from 20 to 100 mg/kg are most preferred. In general, the active compounds are preferably administered at a concentration that will afford effective results without causing any unduly harmful or deleterious side effects, and can be administered either as a single unit dose, or if desired, in convenient subunits administered at suitable times throughout the day.

Also disclosed herein is a method of treating asthma, particularly non-steroid dependent asthma, by administering to a subject in need of such treatment dehydroepiandrosterone (DHEA), an analog thereof, or a pharmaceutically acceptable salt thereof, in an amount effective to inhibit or control asthma to that subject. Examples of DHEA and analogs thereof that may be used to carry out this method are represented by the formula:

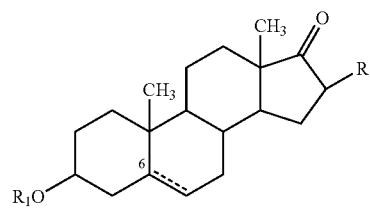

wherein:

the broken line represents an optional double bond;

R is hydrogen or a halogen;

$R_1$ is hydrogen or an $SO_2OM$ group where M is hydrogen, M is sodium, M is a sulphatide group:

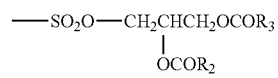

M is a phosphatide group:

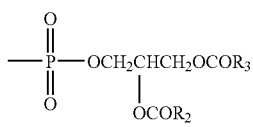

wherein each of $R_2$ and $R_3$, which may be the same or different, is a straight or branched chain alkyl radical of 1 to 14 carbon atoms, or a glucuronide group:

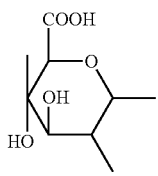

The hydrogen atom at position 5 of Formula I is present in the alpha or beta configuration or the compound comprises a mixture of both configurations. Compounds illustrative of Formula (I) above include:

DHEA, wherein R and $R_1$ are each hydrogen and the double bond is present;

16-alpha bromoepiandrosterone, wherein R is Br, $R_1$ is H and the double bond is present;

16-alpha-fluoroepiandrosterone, wherein R is F, $R_1$ is H and the double bond is present;

etiocholanolone, wherein R and $R_1$ are each hydrogen and the double bond is absent;

dehydroepiandrosterone sulphate, wherein R is H, $R_1$ is $SO_2OM$ and M is a sulphatide group as defined above, and the double bond is absent.

Preferably, in the compound of Formula I, R is halogen (e.g., bromo, chloro, or fluoro), $R_1$ is Hydrogen, and the double bond is present. Most preferably the compound of Formula I is i6-alpha-fluoroepiandrosterone.

The compounds of Formula I are made in accordance with known procedures or variations thereof that will be apparent to those skilled in the art. See U.S. Pat. No. 4,956,355, UK Patent No. 2,240,472, EPO Patent Appln No. 429,187, PCT Patent Appln No. 91/04030; see also M. Abou-Gharbia et al., J. Pharm. Sci. 70, 1154-1157 (1981), Merck Index Monograph No. 7710 (11th ed. 1989).

In some embodiments of the invention, the active agent can be an epiandrosterone analog or derivative thereof. Also, pro-drugs and active metabolites of epiandrosterone are encompassed by the present invention. Those of skill in the art will recognize that the compounds described herein may exhibit the phenomena of tautomerism, conformational isomerism, geometric isomerism and/or optical isomerism. It should be understood that the invention encompasses any tautomeric, conformational isomeric, optical isomeric, and/or geometric isomeric forms of the compounds having one or more of the utilities described herein, as well as mixtures of these various different forms.

Metabolites of epiandrosterones, such as those described in the following references maybe used as the first active agent—Capillary gas chromatography of urinary steroids of terbutaline-treated asthmatic children, Chromatographia (1998), 48(1/2), 163-165; Androstenedione metabolism in human lung fibroblasts; Journal of Steroid Biochemistry (1986), 24(4), 893-7; Metabolism of androsterone and 5α-an-drostane-3α,17β-diol in human lung tissue and in pulmonary endothelial cells in culture, Journal of Clinical Endocrinology and Metabolism (1985), 60(2), 244-50; Testosterone metabolism by human lung tissue, Journal of Steroid Biochemistry (1978), 9(1), 29-32; Metabolism of androsterone and 5 alpha-androstane-3 alpha, 17 beta-diol in human lung tissue and in pulmonary endothelial cells in culture, Journal of clinical endocrinology and metabolism (1985 February), 60(2), 44-50; Metabolism of dehydroisoandrosterone and androstenedione in human pulmonary endothelial cells in culture, Journal of clinical endocrinology and metabolism (1983 May), 56(5), 930-5; Metabolism of dehydroisoandrosterone and androstenedione by the human lung in vitro, Journal of steroid biochemistry (1977 April), 8(4), 277-84; and Testosterone metabolism in dog lung in vitro, Steroids and lipids research (1973), 4(1), 17-23, which references are herein incorporated by reference in their entirety.

Other suitable analogs of DHEA that can be used as the active agent are described herein. FIG. 1 depicts certain suitable analogs of DHEA, including compounds of the Formulas IA, IB, IC, and ID. In the depiction of suitable R groups herein, the attachment point is indicated by a—CH2 group or by an atom marked with an asterisk. R1 and R3 can be linear or branched alkyls including benzyl and optionally substituted alkyls, such as arninoalkyls, hydroxyalkyls, ethers, and carboxylic acids, and optionally substituted aryl and heteroaryls. R1 and R3 can be, for example,

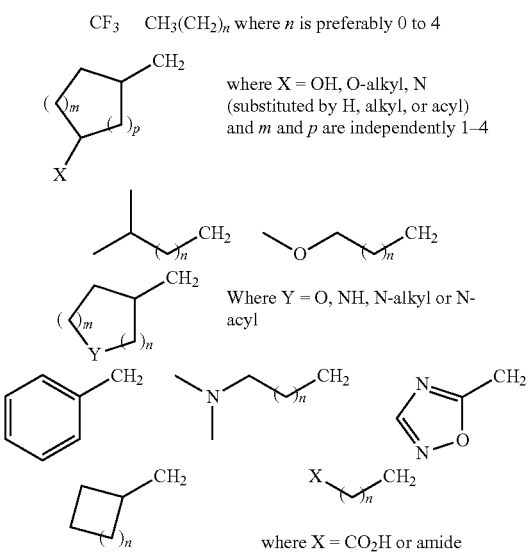

Examples of compounds of formula IA include,

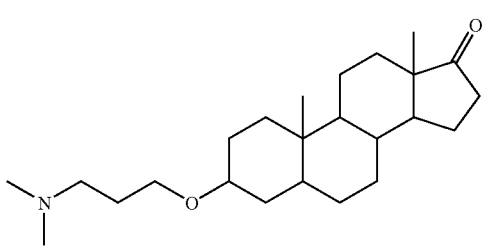

-continued

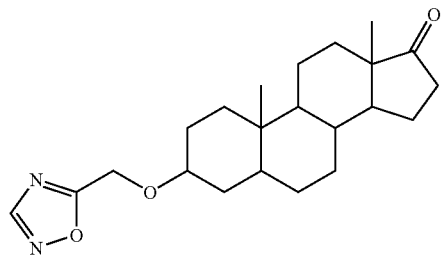

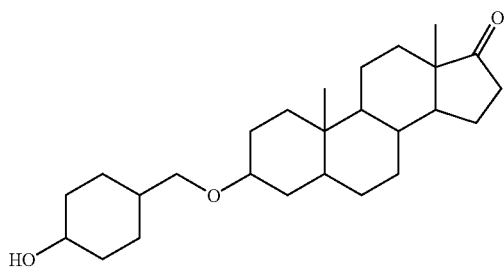

R2 is preferably a diacid-derived or amino acid derived substituent, potentially including chloracetyl derivatives and acrylate derivatives, or optionally substituted aryls such as benzyl and heterobenzoyl. Examples of compounds of formula IB include,

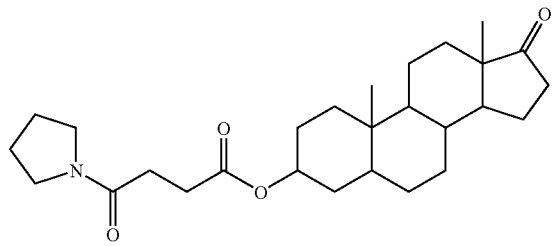

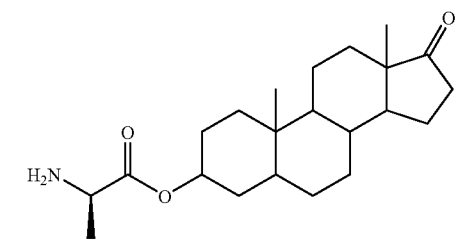

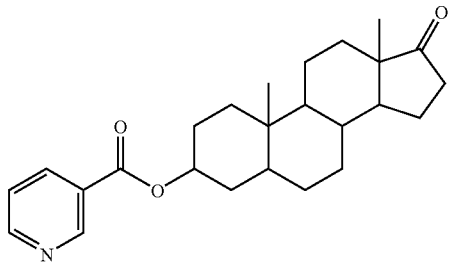

Examples of compounds of formula IC include,

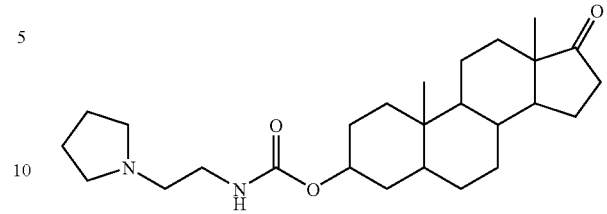

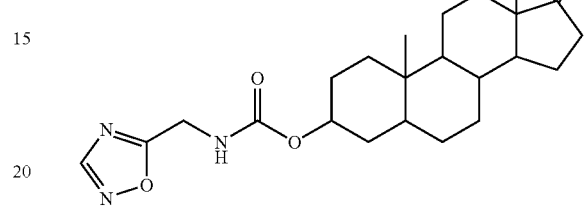

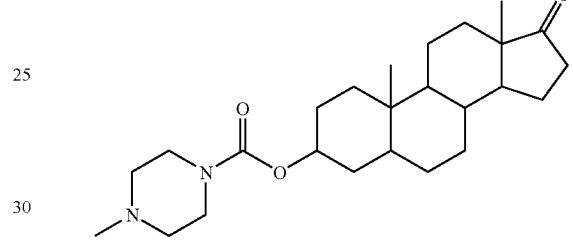

R4 can be aromatic in nature and examples of suitable compounds of formula ID include,

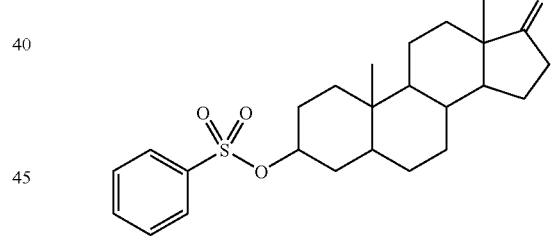

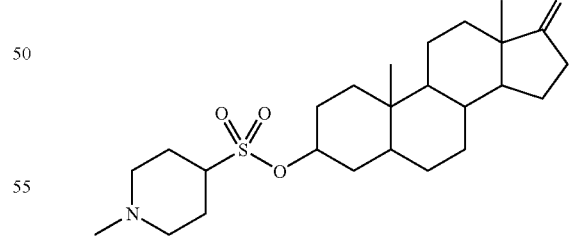

Figure 2:
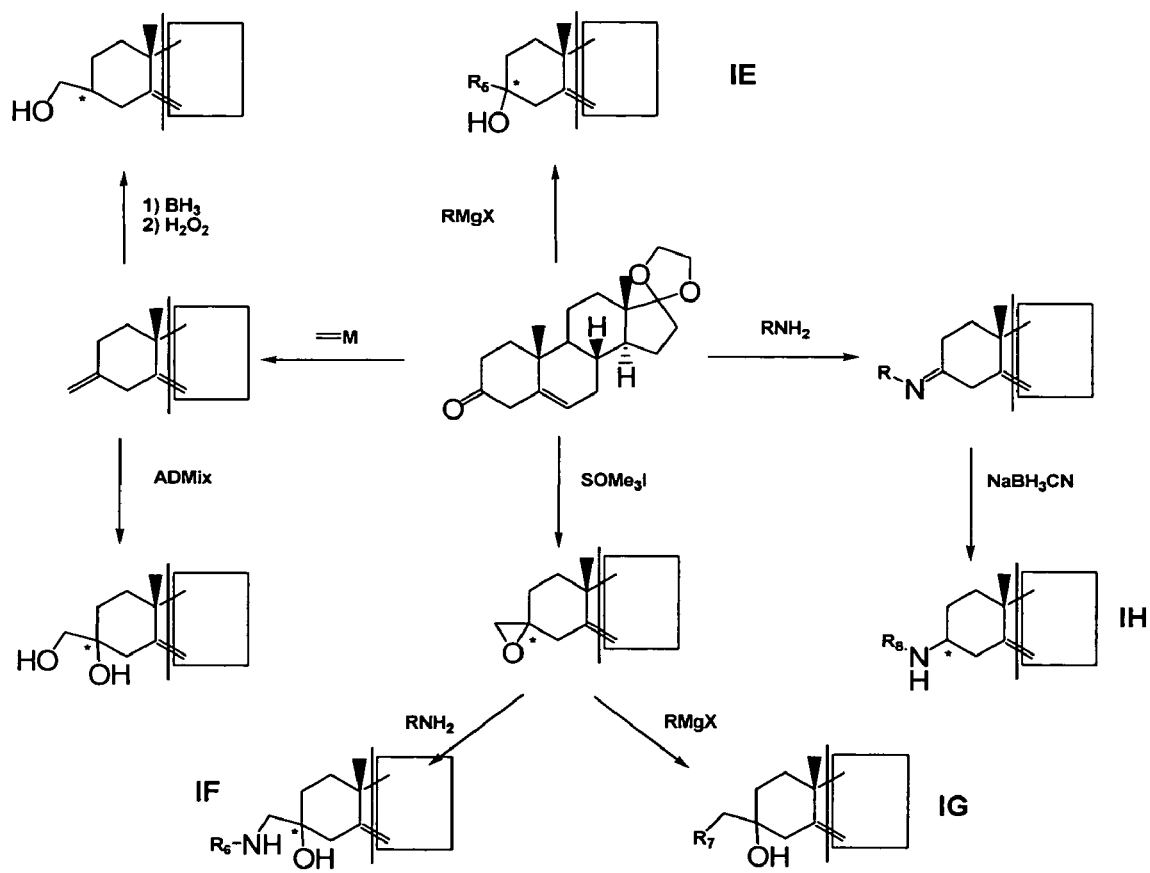
FIG. 2 depicts certain suitable analogs of DHEA.

Other suitable analogs include the analogs wherein modifications have been performed at C-3 position by retaining OH or replacing OH with NH. These analogs are typically made by starting from C-17 acetal protected andrst-4-ene3, 17-dione, such as depicted in FIG. 2. Compounds of Formula IE can be derived from Grignard reagents and possibly aryl-lithium reagents, such as aromatic in nature, and can also be alkynyl, alkenyl, and alkyl. Examples of R5 are $CH_3(CH_2)_n$ where n=0 to 4

Examples of compounds of Formula IE include

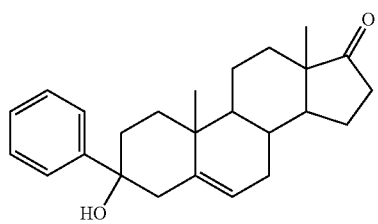

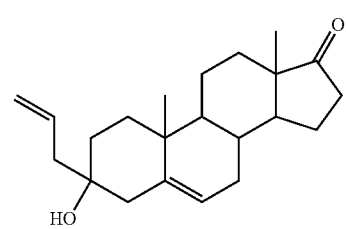

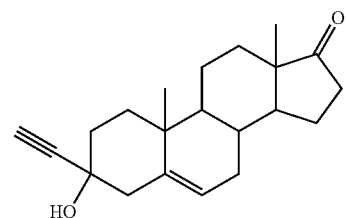

R6 and R8 can independently be a diverse set of amines and can include amines possessing the functionalities as described for the R1 group. Examples of suitable compounds of Formula IF include,

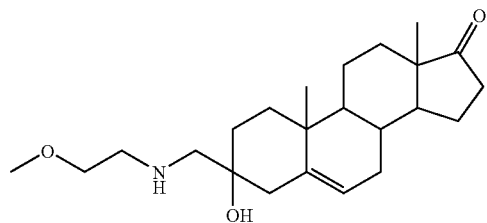

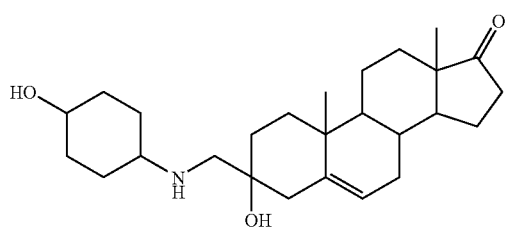

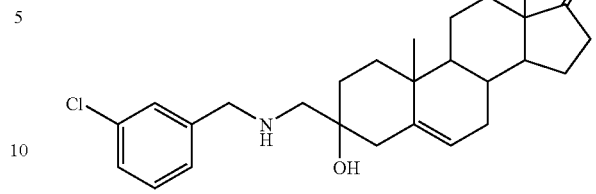

Suitable R7 groups can be derived from Grignard/organolithium reagents and so could encompass the functionalities described for R5. Examples of compounds of Formula IG include

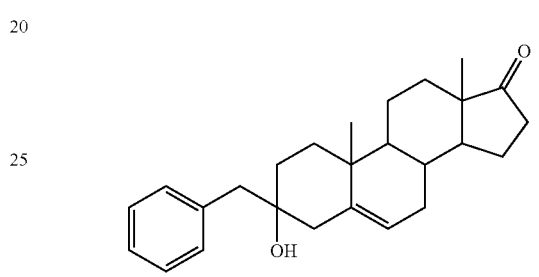

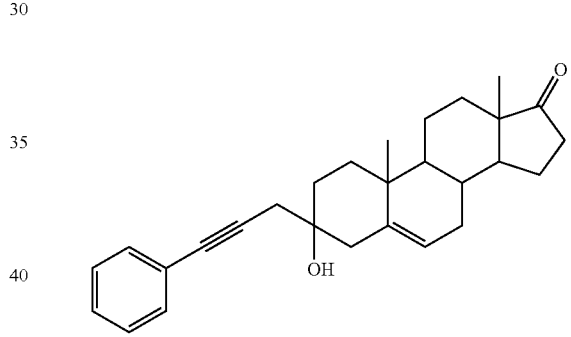

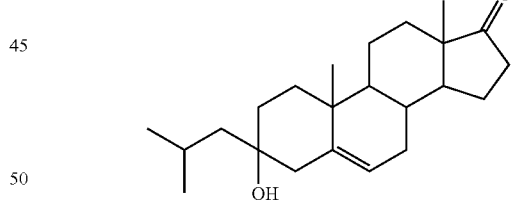

Examples of compounds of Formula IH include

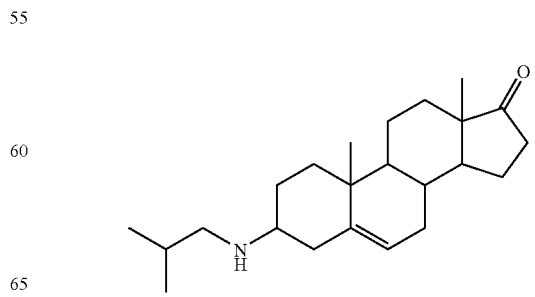

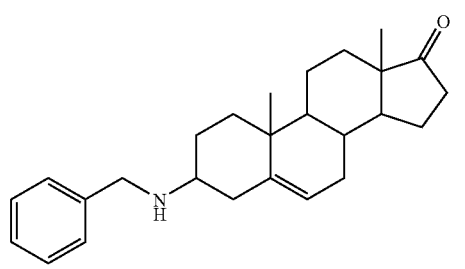

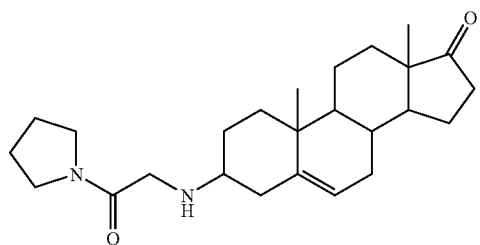

Figure 3:
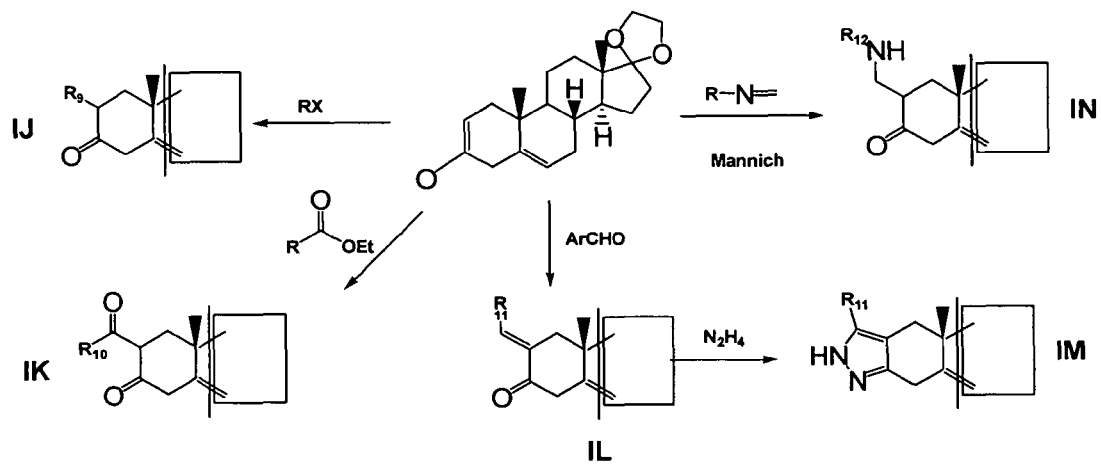
FIG. 3 depicts certain suitable analogs of DHEA.

Other suitable analogs include those compounds wherein the C-2 position of DHEA was modified. Suitable modifications are depicted in FIG. 3. R9 can be derived from alkylating agents, such as alkyl, benzyl, heterobenzyl, and derivatives of other activated halides. Examples of R9 include,

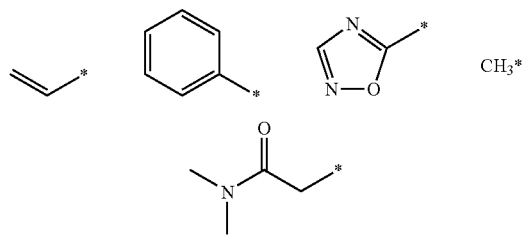

Examples of Formula IJ compounds include,

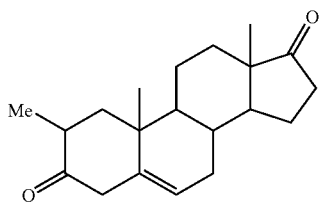

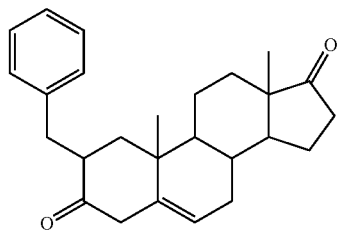

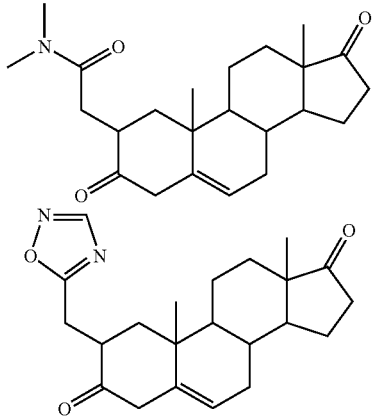

R10 can be aromatic esters such as with aryl or heteroaryl ring or enolisable alkyl esters.

Examples of compounds of formula IK include,

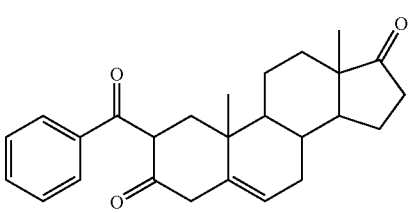

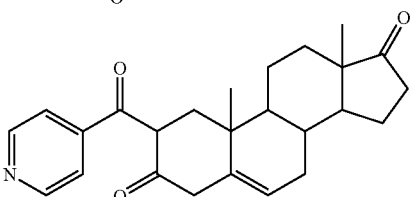

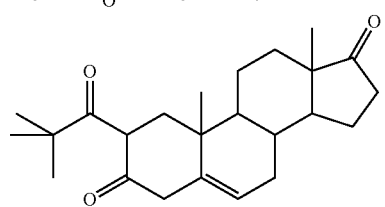

R11 can be a series of aromatic and heteroaromatic aldehydes such as benzene carboxaldehyde and substituted variants thereof, pyridine carboxaldehyde or non-enolisable aldehydes such as (CH3)3CCH=O. Examples of compounds of Formula IL include,

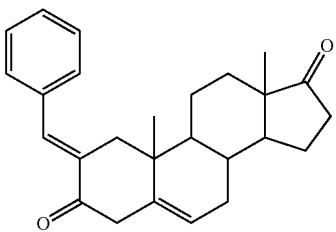

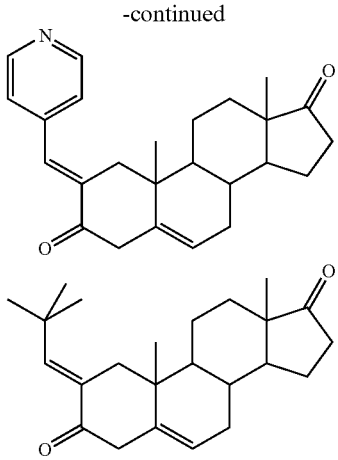

R12 can be a subset of an amine such as for R6. Examples of compounds of formula IN include,

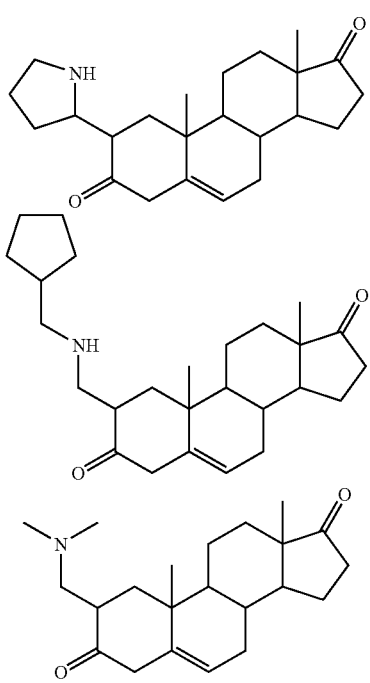

Figure 4:
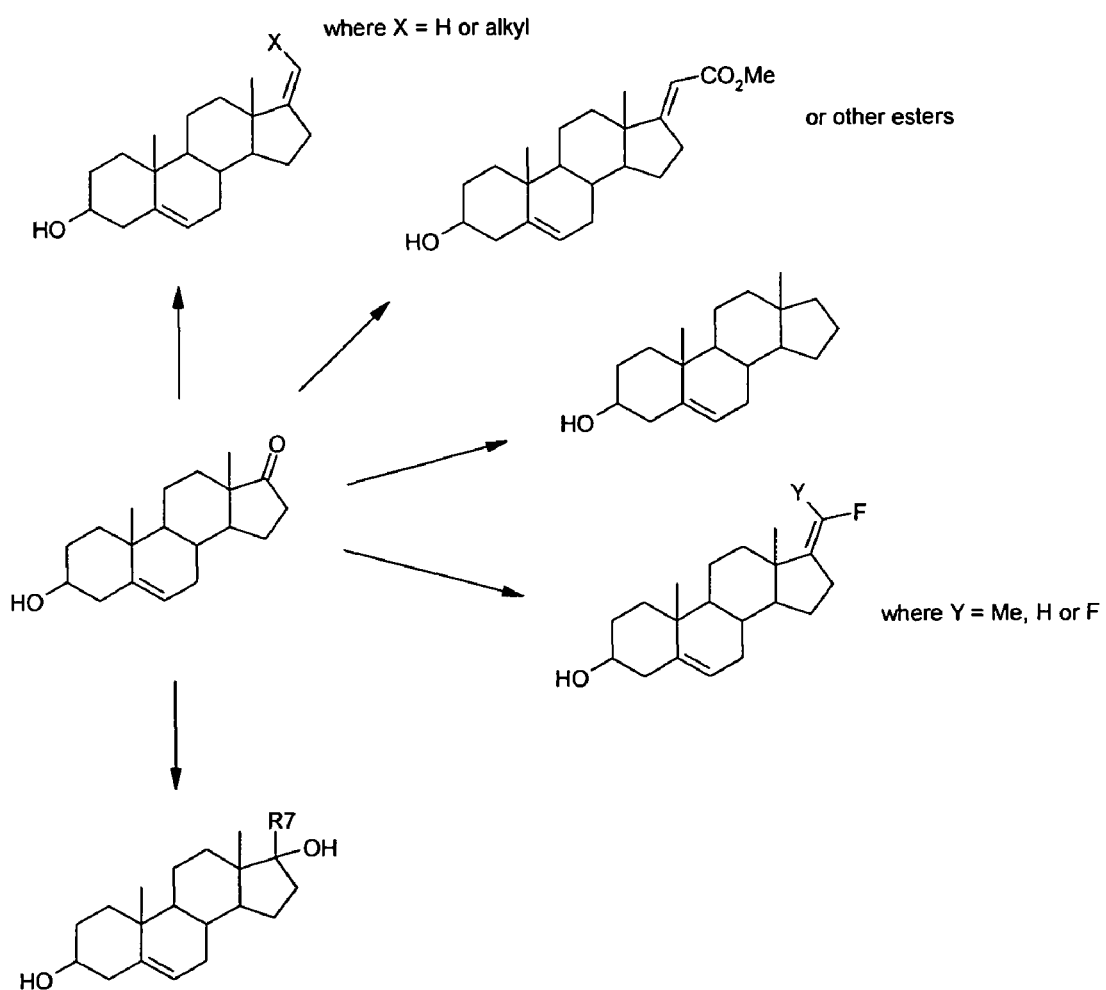
FIG. 4 depicts suitable modifications of the C-17 ketone of DHEA.

Suitable modifications of the C-17 ketone of DHEA are depicted in FIG. 4. The compounds depicted in FIG. 4 can also be used as the active agent.

Other suitable DHEA analogs are described in U.S. Pat. No. 6,635,629; European Patent 934745; Dehydroepiandrosterone and analogs inhibit DNA binding of AP-1 and airway smooth muscle proliferation, Journal of Pharmacology and Experimental Therapeutics (1998), 285(2), 876-883; and Dehydroepiandrosterone and related steroids inhibit mitochondrial respiration in vitro, International Journal of Biochemistry (1989), 21(10), 1103-7, all of which are herein incorporated by reference in their entirety.

The compounds used to treat asthma may be administered per se or in the form of pharmaceutically acceptable salts, as discussed above (the two together again being referred to as "active compounds"). The active compounds salts may be administered either systemically, as discussed above, or to the lungs of the subject as discussed below. In general, the active compounds salts are administered in a dosage of 1 to 3600 mg/kg body weight, more preferably about 5 to 1800 mg/kg, and most preferably about 20 to 100 mg/kg. The active compounds may be administered once or several times a day.

The active compounds disclosed herein may be administered to the lungs of a subject by any suitable means, but are preferably administered by generating an aerosol comprised of respirable particles, the respirable particles comprised of the active compound, which particles the subject inhales (i.e., by inhalation administration). The respirable particles may be liquid or solid.

Particles comprised of active compound for practicing the present invention should include particles of respirable size: that is, particles of a size sufficiently small to pass through the mouth and larynx upon inhalation and into the bronchi and alveoli of the lungs. In general, particles ranging from about 0.5 to 10 microns in size (more particularly, less than about 5 microns in size) are respirable. Particles of non-respirable size which are included in the aerosol tend to deposit in the throat and be swallowed, and the quantity of non-respirable particles in the aerosol is preferably minimized. For nasal administration, a particle size in the range of 10-500 μm is preferred to ensure retention in the nasal cavity.

Liquid pharmaceutical compositions of active compound for producing an aerosol can be prepared by combining the active compound with a suitable vehicle, such as sterile pyrogen free water. Solid particulate compositions containing respirable dry particles of micronized active compound may be prepared by grinding dry active compound with a mortar and pestle, and then passing the micronized composition through a 400 mesh screen to break up or separate out large agglomerates. A solid particulate composition comprised of the active compound may optionally contain a dispersant which serves to facilitate the formation of an aerosol. A suitable dispersant is lactose, which may be blended with the active compound in any suitable ratio (e.g., a 1 to 1 ratio by weight).

Aerosols of liquid particles comprising the active compound may be produced by any suitable means, such as with a nebulizer. See, e.g., U.S. Pat. No. 4,501,729. Nebulizers are commercially available devices which transform solutions or suspensions of the active ingredient into a therapeutic aerosol mist either by means of acceleration of a compressed gas, typically air or oxygen, through a narrow venturi orifice or by means of ultrasonic agitation. Suitable compositions for use in nebulizers consist of the active ingredient in a liquid carrier, the active ingredient comprising up to 40% w/w of the compositions, but preferably less than 20% w/w. The carrier is typically water or a dilute aqueous alcoholic solution, preferably made isotonic with body fluids by the addition of, for example, sodium chloride. Optional additives include preservatives if the compositions is not prepared sterile, for example, methyl hydroxybenzoate, antioxidants, flavoring agents, volatile oils, buffering agents and surfactants.

Aerosols of solid particles comprising the active compound may likewise be produced with any solid particulate medicament aerosol generator. Aerosol generators for administering solid particulate medicaments to a subject produce particles which are respirable, as explained above, and generate a volume of aerosol containing a predetermined metered dose of a medicament at a rate suitable for human administration. Examples of such aerosol generators include metered dose inhalers and insufflators.

Ubiquinone may be administered concurrently with the DHEA or analog thereof in the methods of treating asthma described above. The phrase "concurrently administering," as used herein, means that the DHEA or the DHEA analog are administered either (a) simultaneously in time (preferably by formulating the two together in a common pharmaceutical carrier), or (b) at different times during the course of a common treatment schedule. In the latter case, the two compounds are administered at times sufficiently close for the ubiquinone to ubiquinone depletion in the lungs (and heart) of the subject and thereby counterbalance any deterioration of lung (and heart) function that may result from the administration of the DHEA or the analog thereof. The term "ubiquinone", as used herein, refers to a family of compounds having structures based on a 2,3-dimethoxy-5-methylbenzoquinone nucleus with a variable terpenoid acid chain containing on to twelve mono-unsaturated trans-isoprenoid units. Such compounds are known in the art as "Coenzyme $Q_n$", in which n equals 1 to 12. These compounds may be referred to herein as compounds represented by the formula:

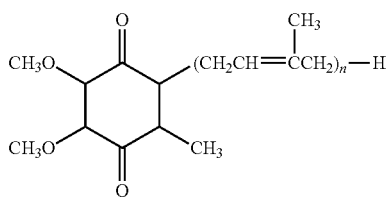

wherein n=1 to 10. Preferably, in the method of the invention, the ubiquinone is a compound according to formula given above, wherein n=6 to 10 (e.g., Coenzymes $Q_{6-10}$), and most preferably wherein n=10 (i.e., Coenzyme $Q_{10}$).

Where the ubiquinone is formulated with a pharmaceutically acceptable carrier separately from the DHEA, analog thereof, or salt thereof (e.g., where the DHEA, analog thereof or salt thereof is administered to the lungs of the subject, and the ubiquinone is administered systemically) it may be formulated by any of the techniques set forth above.

In general, the ubiquinone is administered in an amount effective to offset ubiquinone depletion in the lungs and heart of the subject induced by the DHEA, analog thereof, or salt thereof, and the dosage will vary depending upon the condition of the subject and the route of administration. The ubiquinone is preferably administered in a total amount per day of about 1 to 1200 mg/kg body weight, more preferably about 30 to 600 mg/kg, and most preferably about 50b to 150 mg/kg. The ubiquinone may be administered once or several times a day.

The following examples are provided to more fully illustrate the present invention and should not be construed as restrictive thereof. In the following examples, DHEA means dehydroepiandrosterone, s means seconds, mg means milligrams, kg means kilograms, kW means kilowatts, MHz means megahertz, and nmol means nanomoles.

EXAMPLES 1 AND 2

Effects of Folinic Acid and DHEA on Adenosine Levels In vivo

Young adult male Fischer 344 rats (120 grams) were administered dehydroepiandrosterone (DHEA) (300 mg/kg) or methyltestosterone (40 mg/kg) in carboxymethylcellulose by gavage once daily for fourteen days. Folinic acid (50 mg/kg) was administered intraperitoneally once daily for fourteen days. On the fifteenth day, the animals were sacrificed by microwave pulse (1.33 kW, 2450 MHz, 6.5 s) to the cranium, which instantly denatures all brain protein and prevents further metabolism of adenosine. Hearts were removed from animals and flash frozen in liquid nitrogen within 10 seconds of death. Liver and lungs were removed en bloc and flash frozen within 30 seconds of death. Brain tissue was subsequently dissected. Tissue adenosine was extracted, derivatized to 1, $N^6$-ethenoadenosine and analyzed by high performance liquid chromatography (HPLC) using spectrofluorometric detection according to the method of Clark and Dar (J. of Neuroscience Methods 25:243 (1988)). Results of these experiments are summarized in Table 1 below. Results are expressed as the mean±SEM, with $\chi p<0.05$ compared to control group and $\phi p<0.05$ compared to DHEA or methyltestosterone-treated groups.

TABLE 1

Effects of DHEA, ó-1-methyltestosterone and folinic acid on adenosine levels in various tissues of the rat.

| | Intracellular adenosine (nmols)/mg protein | | | |
|---|---|---|---|---|
| Treatment | Heart | Liver | Lung | Brain |
| Control | 10.6 ± 0.6 | 14.5 ± 1.0 | 3.1 ± 0.2 | 0.5 ± 0.04 |
| | (n = 12) | (n = 12) | (n = 6) | (n = 12) |
| DHEA (300 mg/kg) | 6.7 ± 0.5 (n = 12) ψ | 16.4 ± 1.4 (n = 12) | 2.3 ± 0.3 (n = 6) ψ | 0.19 ± 0.01 (n = 12) ψ |
| Methyltestosterone (40 mg/kg) | 8.3 ± 1.0 (n = 6) ψ | 16.5 ± 0.9 (n = 6) | N.D. | 0.42 ± 0.06 (n = 6) |
| Methyltestosterone (120 mg/kg) | 6.0 ± 0.4 (n = 6) ψ | 5.1 ± 0.5 (n = 6) ψ | N.D. | 0.32 ± 0.03 (n = 6) ψ |
| Folinic Acid (50 mg/kg) | 12.4 ± 2.1 (n = 5) | 16.4 ± 2.4 (n = 5) | N.D. | 0.72 ± 0.09 (n = 5) ψ |
| DHEA (300 mg/kg) + Folinic Acid (50 mg/kg) | 11.1 ± 0.6 (n = 5) φ | 18.8 ± 1.5 (n = 5) φ | N.D. | 0.55 ± 0.09 (n = 5) φ |
| Methyltestosterone (120 mg/kg) + Folinic Acid (50 mg/kg) | 9.1 ± 0.4 (n = 6) φ | N.D. | N.D. | 0.60 ± 0.06 (n = 6) φ |

The results of these experiments indicate that rats administered DHEA or methyltestosterone daily for two weeks showed multi-organ depletion of adenosine. Depletion was dramatic in brain (60% depletion for DHEA, 34% for high dose methyltestosterone) and heart (37% depletion for DHEA, 22% depletion for high dose methyltestosterone). Co-administration of folinic acid completely abrogated steroid-mediated adenosine depletion. Folinic acid administered alone induce increases in adenosine levels for all organs studied.

The foregoing examples are illustrative of the present invention, and are not to be construed as limiting thereof. The invention is defined by the following claims, with equivalents of the claims to be included therein.

That which is claimed is:

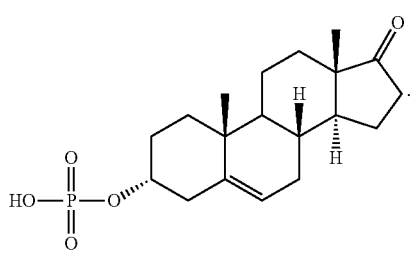

1. A method of treatment of asthma, comprising administering to a subject in need of such treatment of a therapeutically effective amount of a pharmaceutical composition comprising a compound of formula I, or pharmaceutically or veterinarily acceptable salts thereof, to treat or reduce the likelihood of asthma